(12) United States Patent
Lind et al.

(10) Patent No.: US 10,246,485 B2
(45) Date of Patent: Apr. 2, 2019

(54) METHOD TO CONCENTRATE VON WILLEBRAND FACTOR OR COMPLEXES THEREOF

(71) Applicant: CSL LIMITED, Parkville, Victoria (AU)

(72) Inventors: Holger Lind, Marburg (DE); Sonja Beckmann-Scheld, Marburg (DE); Katharina Propp, Nieder-Ohmen (DE)

(73) Assignee: CSL LIMITED, Parkville (AU)

( * ) Notice: Subject to any disclaimer, the term of this patent is extended or adjusted under 35 U.S.C. 154(b) by 59 days.

(21) Appl. No.: 15/034,907

(22) PCT Filed: Nov. 7, 2014

(86) PCT No.: PCT/AU2014/050340
§ 371 (c)(1),
(2) Date: May 6, 2016

(87) PCT Pub. No.: WO2015/066769
PCT Pub. Date: May 14, 2015

(65) Prior Publication Data
US 2016/0289267 A1    Oct. 6, 2016

(30) Foreign Application Priority Data

Nov. 8, 2013 (EP) ................................. 13192189

(51) Int. Cl.
| | |
|---|---|
| *C07K 1/00* | (2006.01) |
| *C07K 14/00* | (2006.01) |
| *C07K 16/00* | (2006.01) |
| *C07K 17/00* | (2006.01) |
| *A23J 1/00* | (2006.01) |
| *A61K 35/14* | (2015.01) |
| *A61K 38/00* | (2006.01) |
| *C07K 1/32* | (2006.01) |
| *A61K 38/36* | (2006.01) |
| *A61K 38/37* | (2006.01) |
| *C07K 14/755* | (2006.01) |
| *C07K 14/76* | (2006.01) |

(52) U.S. Cl.
CPC ............... *C07K 1/32* (2013.01); *A61K 38/36* (2013.01); *A61K 38/37* (2013.01); *C07K 14/755* (2013.01); *C07K 14/76* (2013.01); *C07K 2319/31* (2013.01)

(58) Field of Classification Search
None
See application file for complete search history.

(56) References Cited

U.S. PATENT DOCUMENTS

| 5,408,039 A | 4/1995 | Burnouf-Radosevich et al. |
| 5,679,776 A | 10/1997 | Burnouf-Radosevich et al. |
| 5,688,912 A * | 11/1997 | Dadd .................... C07K 14/001 530/329 |
| 5,760,189 A * | 6/1998 | Vicik ....................... C07K 1/18 530/412 |
| 5,869,617 A | 2/1999 | Fischer et al. |
| 7,659,247 B2 | 2/2010 | Kretschmar et al. |
| 2002/0019036 A1 * | 2/2002 | Schwarz .............. C07K 14/755 435/174 |
| 2004/0132654 A1 | 7/2004 | Kumpe et al. |
| 2005/0239171 A1 | 10/2005 | Mitterer et al. |
| 2010/0305305 A1 * | 12/2010 | Poulle ................. C07K 14/755 530/383 |
| 2016/0272675 A1 * | 9/2016 | Jungbauer .............. C07K 16/00 |

FOREIGN PATENT DOCUMENTS

| EP | 0 503 991 A1 | 9/1992 |
| EP | 0 784 632 B1 | 1/1999 |
| EP | 1 405 863 A1 | 4/2004 |
| EP | 1522312 A1 * | 4/2005 ............ A61K 38/37 |
| EP | 2 078 730 A1 | 7/2009 |
| WO | WO 96/10584 | 4/1996 |
| WO | WO 2009/156137 A1 | 12/2009 |
| WO | WO 2010/025278 A1 | 3/2010 |

OTHER PUBLICATIONS

Oasis Fine Chem., "Sodium Chemicals," available online at http://www.oasisfinechem.com/sodium-chemicals.html, 20 pages (first available on Mar. 24, 2013).*
"Contact." Merriam-Webster.com. Merriam-Webster, n.d. Web. Nov. 29, 2017.*
Collins et al., 1987. "Molecular cloning of the human gene for von Willebrand factor and identification of the transcription initiation site," Proc. Natl. Acad. Sci. USA, vol. 84, 4393-4397.
European Search Report 13192189.2-1456, dated Apr. 4, 2014 (5 pages).
Federici et al., 2004. "A sensitive ristocetin co-factor activity assay with recombinant glycoprotein Ibα for the diagnosis of patients with low von Willebrand factor levels," Haematologica, vol. 89, 77-85.
Fischer et al., 1994. "Structural analysis of recombinant von Willebrand factor: identification of hetero-and homo-dimers," FEBS Letters, vol. 351, 345-348.
Green et al., 2008. "Measurement of Hemostatic Factors in EDTA Plasma," Am. J. Clin. Pathol., vol. 130, 811-815.
Kallas et al., 2001. "The von Willebrand factor collagen-binding activity assay: clinical application," Ann Hematol, vol. 80, 466-471.
Sucker et al., 2006. "Determination of von Willebrand Factor Activity: Evaluation of the HaemosIL™ Assay in Comparison with established procedures," Clinical and Applied Thrombosis/Hemostasis, vol. 12, 305-310.
PCT Search Report and Written Opinion PCT/AU2014/050340, dated Jan. 14, 2015 (9 pages).

* cited by examiner

*Primary Examiner* — James H Alstrum-Acevedo
*Assistant Examiner* — Thea D' Ambrosio
(74) *Attorney, Agent, or Firm* — Finnegan, Henderson, Farabow, Garrett & Dunner, L.L.P.

(57) ABSTRACT

The present invention relates to a method for concentrating von Willebrand Factor (VWF) from an aqueous solution comprising precipitating the VWF by providing calcium ions and phosphate ions and the subsequent resolubilization of the VWF by means of an aqueous solution comprising a calcium complexing compound.

10 Claims, No Drawings

METHOD TO CONCENTRATE VON WILLEBRAND FACTOR OR COMPLEXES THEREOF

CROSS-REFERENCE TO RELATED APPLICATIONS

This application is the United States national stage entry under 35 U.S.C. § 371 of International Application No. PCT/AU2014/050340, filed on Nov. 7, 2014 and published as WO 2015/066769 A1, which claims priority to European Patent Application No. 13192189.2, filed on Nov. 8, 2013. The contents of these applications are each incorporated herein by reference in their entirety.

FIELD OF THE INVENTION

The present invention relates to a method for concentrating von Willebrand Factor (VWF) from an aqueous solution comprising precipitating the VWF by providing calcium ions and phosphate ions and the subsequent resolubilization of the VWF by means of an aqueous solution comprising a calcium complexing compound.

BACKGROUND OF THE INVENTION

One of the most prevalent bleeding disorders is von Willebrand's disease (VWD), which is caused by missing von Willebrand factor (VWF), reduced levels of VWF or the expression of VWF variants with functional defects.

VWF is one of the largest known plasma proteins. VWF is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant Factor VIII. VWF is synthesized in endothelial cells and megakaryocytes as a 2813 amino acid precursor molecule. The amino acid sequence and the cDNA sequence of wild-type VWF are disclosed in Collins et al. 1987, Proc Natl. Acad. Sci. USA 84:4393-4397. The precursor polypeptide, pre-pro-VWF, consists of a 22-residue signal peptide, a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. More important, VWF dimers are multimerized via N-terminal disulfide bridges and the propeptide of 741 amino acids length is cleaved off by the enzyme PACE/furin in the late Golgi apparatus. The propeptide as well as the high-molecular-weight multimers of VWF (VWF-HMWM) are stored in the Weibel-Pallade bodies of endothelial cells or in the α-Granules of platelets.

Once secreted into plasma the protease ADAMTS13 cleaves VWF within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCo/VWF antigen, the higher the relative amount of high molecular weight multimers.

Defects in VWF are causal to VWD 0, which is characterized by a more or less pronounced bleeding phenotype. VWD type 3 is the most severe form in which VWF is completely missing, VWD type 1 relates to a quantitative loss of VWF and its phenotype can be very mild. VWD type 2 relates to qualitative defects of VWF and can be as severe as VWD type 3. VWD type 2 has many sub forms some of them being associated with the loss or the decrease of high molecular weight multimers. Von VWD type 2a is characterized by a loss of both intermediate and large multimers. VWD type 2B is characterized by a loss of highest-molecular-weight multimers.

VWD is the most frequently inherited bleeding disorder in humans and can be treated by replacement therapy with concentrates containing VWF of plasmatic or recombinant origin. VWF can be prepared from human plasma as for example described in EP 0503991. EP 0784632 describes a method for isolating recombinant VWF.

In plasma Factor VIII binds with high affinity to von VWF, which binding protects Factor VIII from premature catabolism and VWF thus plays in addition to its role in primary hemostasis a crucial role to regulate plasma levels of Factor VIII and as a consequence is also a central factor to control secondary hemostasis.

Recombinant or plasma derived VWF or VWF/Factor VIII complexes are used to provide pharmaceutical preparations to treat VWD and VWF/Factor VIII complexes have been also used to treat the medical indication hemophilia A in which disease Factor VIII is either missing or only available in reduced concentrations or as a Factor VIII variant with reduced functionality.

In order to provide such pharmaceutical preparations there is a need for efficient and scalable purification methods for VWF.

Due to its enormous size VWF multimers are especially sensitive to shear stress. Already at a sheer stress of above 2000 sec$^{-1}$ VWF multimers begin to unfold and the unfolded VWF is then prone to degradation and denaturation. Common methods to concentrate therapeutic proteins in industrial manufacturing processes like ultrafiltration are not suitable to concentrate VWF in industrial scale manufacturing because they exert too high sheer stress. WO 2010/025278 offers one technical solution to achieve the concentration of VWF without compromising its specific activity using hollow fibre membranes, but there is a need to identify alternative technologies to concentrate VWF from solutions comprising VWF which are simpler, cheaper and scalable while preserving the structural integrity and biological activity of this complex macromolecule.

Precipitation of proteins is a technique known in the prior art. However, for each given protein the optimal precipitation agent and precipitation parameters must be identified. One way how precipitation can be achieved is by salting out procedures (for example by using ammonium sulphate) where the ionic components of the salt used for the precipitation compete with the target protein for water molecules and if the concentration of the salt ions is high enough, the target protein becomes insufficiently hydrated to be kept in solution leading to the precipitation of the target protein. However precipitates obtained by salting out procedures are often difficult to resolubilize. Therefore a need exists to find methods to precipitate VWF which allow an easy and gentle resolubilization, while preserving the structural integrity and biological activity of VWF.

Also precipitation is often carried out as a co-precipitation, where the precipitating agent also precipitates with the protein of interest. Depending on the nature of the precipitating agent the target protein must then be purified from the precipitating agent, such that the target protein is not contaminated by the precipitating agent. Powerful precipitating agents like synthetic polyelectrolytes can be very difficult or slow to remove and release from the target protein.

Precipitation of vWF with a combination of glycine and sodium chloride have also been described in the prior art (EP1405863). However, high amounts of salts are needed and it is difficult to avoid the unwanted precipitation of other components from the solution than the target protein. If for example the VWF solution still contains a surfactant like pluronic acid which commonly used in cell culture media, precipitation conditions as described in EP1405863 may lead to the co-precipitation of pluronic acid which may even comprise the precipitation of the target protein.

U.S. Pat. No. 5,679,776 discloses the use of 80 mM barium chloride in order to remove prothrombin complex from a solution of VWF complexed to Factor VIII by way of precipitating the prothrombin complex but not the VWF/Factor VIII complex. Surprisingly it was now found that a combination of calcium ions—which is like barium an alkaline earth metal—with phosphate ions can be used to precipitate VWF in high yield, which precipitate can then be resolubilized under gentle conditions with a calcium complexing agent while retaining the biological activity of VWF.

DESCRIPTION OF THE INVENTION

It is an objective of this invention to provide a method for concentrating VWF from an aqueous solution comprising the steps of
(a) precipitating VWF by providing calcium ions and phosphate ions to the aqueous solution,
(b) separating the precipitate formed in step (a) from the aqueous solution,
(c) resolubilizing the precipitate isolated in step (b) by means of an aqueous solution comprising a calcium complexing agent.

DETAILED DESCRIPTION OF THE INVENTION

The invention pertains to a method for concentrating von VWF by precipitating VWF from an aqueous solution by contacting said aqueous solution with calcium ions and phosphate ions leading to the precipitation of the VWF and calcium phosphate. The precipitate comprising the VWF is separated from the aqueous solution and resolubilized under gentle conditions retaining the biological activity of VWF by adding an aqueous solution to the precipitate which comprises a calcium complexing agent.

In preferred embodiments the invention pertains to a method for concentrating von Willebrand Factor (VWF) from an aqueous solution comprising the steps of
(a) precipitating the VWF by providing calcium ions and phosphate ions to the aqueous solution,
(b) separating the precipitate formed in step (a) from the aqueous solution,
(c) resolubilizing the precipitate isolated in step (b) by means of an aqueous solution comprising a calcium complexing agent.

In preferred embodiments of the invention a concentration of the phosphate ions between at least 1 mM and up to below 10 mM and a concentration of the calcium ions of at least 16 mM is used.

In other preferred embodiments of the invention a concentration of the phosphate ions of at least 10 mM and a concentration of the calcium ions of at least 10 mM is used.

In a preferred embodiment the concentration of the phosphate ions is 5 mM and the concentration of the calcium ions is selected from a range between 50 mM to 60 mM including the endpoints of that range.

Multiple combinations of certain phosphate concentrations can be used in conjunction with certain calcium concentration. For example and without limiting the invention the following combinations of concentrations can be used.

1 mM/L phosphate ions can be combined with 16 mM/L calcium ions.
2 mM/L phosphate ions can be combined with 16 mM/L calcium ions.
3 mM/L phosphate ions can be combined with 16 mM/L calcium ions.
4 mM/L phosphate ions can be combined with 16 mM/L calcium ions.
5 mM/L phosphate ions can be combined with 16 mM/L calcium ions.
6 mM/L phosphate ions can be combined with 16 mM/L calcium ions.
7 mM/L phosphate ions can be combined with 16 mM/L calcium ions.
8 mM/L phosphate ions can be combined with 16 mM/L calcium ions.
9 mM/L phosphate ions can be combined with 16 mM/L calcium ions.
9.5 mM/L phosphate ions can be combined with 16 mM/L calcium ions.
9.9 mM/L phosphate ions can be combined with 16 mM/L calcium ions.
or
1 mM/L phosphate ions can be combined with 20 mM/L calcium ions.
2 mM/L phosphate ions can be combined with 20 mM/L calcium ions.
3 mM/L phosphate ions can be combined with 20 mM/L calcium ions.
4 mM/L phosphate ions can be combined with 20 mM/L calcium ions.
5 mM/L phosphate ions can be combined with 20 mM/L calcium ions.
6 mM/L phosphate ions can be combined with 20 mM/L calcium ions.
7 mM/L phosphate ions can be combined with 20 mM/L calcium ions.
8 mM/L phosphate ions can be combined with 20 mM/L calcium ions.
9 mM/L phosphate ions can be combined with 20 mM/L calcium ions.
9.5 mM/L phosphate ions can be combined with 20 mM/L calcium ions.
9.9 mM/L phosphate ions can be combined with 20 mM/L calcium ions.
or
1 mM/L phosphate ions can be combined with 30 mM/L calcium ions.
2 mM/L phosphate ions can be combined with 30 mM/L calcium ions.
3 mM/L phosphate ions can be combined with 30 mM/L calcium ions.
4 mM/L phosphate ions can be combined with 30 mM/L calcium ions.

5 mM/L phosphate ions can be combined with 30 mM/L calcium ions.
6 mM/L phosphate ions can be combined with 30 mM/L calcium ions.
7 mM/L phosphate ions can be combined with 30 mM/L calcium ions.
8 mM/L phosphate ions can be combined with 30 mM/L calcium ions.
9 mM/L phosphate ions can be combined with 30 mM/L calcium ions.
9.5 mM/L phosphate ions can be combined with 30 mM/L calcium ions.
9.9 mM/L phosphate ions can be combined with 30 mM/L calcium ions.
or
1 mM/L phosphate ions can be combined with 40 mM/L calcium ions.
2 mM/L phosphate ions can be combined with 40 mM/L calcium ions.
3 mM/L phosphate ions can be combined with 40 mM/L calcium ions.
4 mM/L phosphate ions can be combined with 40 mM/L calcium ions.
5 mM/L phosphate ions can be combined with 40 mM/L calcium ions.
6 mM/L phosphate ions can be combined with 40 mM/L calcium ions.
7 mM/L phosphate ions can be combined with 40 mM/L calcium ions.
8 mM/L phosphate ions can be combined with 40 mM/L calcium ions.
9 mM/L phosphate ions can be combined with 40 mM/L calcium ions.
9.5 mM/L phosphate ions can be combined with 40 mM/L calcium ions.
9.9 mM/L phosphate ions can be combined with 40 mM/L calcium ions.
or
1 mM/L phosphate ions can be combined with 50 mM/L calcium ions.
2 mM/L phosphate ions can be combined with 50 mM/L calcium ions.
3 mM/L phosphate ions can be combined with 50 mM/L calcium ions.
4 mM/L phosphate ions can be combined with 50 mM/L calcium ions.
5 mM/L phosphate ions can be combined with 50 mM/L calcium ions.
6 mM/L phosphate ions can be combined with 50 mM/L calcium ions.
7 mM/L phosphate ions can be combined with 50 mM/L calcium ions.
8 mM/L phosphate ions can be combined with 50 mM/L calcium ions.
9 mM/L phosphate ions can be combined with 50 mM/L calcium ions.
9.5 mM/L phosphate ions can be combined with 50 mM/L calcium ions.
9.9 mM/L phosphate ions can be combined with 50 mM/L calcium ions.
or
1 mM/L phosphate ions can be combined with 60 mM/L calcium ions.
2 mM/L phosphate ions can be combined with 60 mM/L calcium ions.
3 mM/L phosphate ions can be combined with 60 mM/L calcium ions.
4 mM/L phosphate ions can be combined with 60 mM/L calcium ions.
5 mM/L phosphate ions can be combined with 60 mM/L calcium ions.
6 mM/L phosphate ions can be combined with 60 mM/L calcium ions.
7 mM/L phosphate ions can be combined with 60 mM/L calcium ions.
8 mM/L phosphate ions can be combined with 60 mM/L calcium ions.
9 mM/L phosphate ions can be combined with 60 mM/L calcium ions.
9.5 mM/L phosphate ions can be combined with 60 mM/L calcium ions.
9.9 mM/L phosphate ions can be combined with 60 mM/L calcium ions.
or
1 mM/L phosphate ions can be combined with 80 mM/L calcium ions.
2 mM/L phosphate ions can be combined with 80 mM/L calcium ions.
3 mM/L phosphate ions can be combined with 80 mM/L calcium ions.
4 mM/L phosphate ions can be combined with 80 mM/L calcium ions.
5 mM/L phosphate ions can be combined with 80 mM/L calcium ions.
6 mM/L phosphate ions can be combined with 80 mM/L calcium ions.
7 mM/L phosphate ions can be combined with 80 mM/L calcium ions.
8 mM/L phosphate ions can be combined with 80 mM/L calcium ions.
9 mM/L phosphate ions can be combined with 80 mM/L calcium ions.
9.5 mM/L phosphate ions can be combined with 80 mM/L calcium ions.
9.9 mM/L phosphate ions can be combined with 80 mM/L calcium ions.
or
1 mM/L phosphate ions can be combined with 100 mM/L calcium ions.
2 mM/L phosphate ions can be combined with 100 mM/L calcium ions.
3 mM/L phosphate ions can be combined with 100 mM/L calcium ions.
4 mM/L phosphate ions can be combined with 100 mM/L calcium ions.
5 mM/L phosphate ions can be combined with 100 mM/L calcium ions.
6 mM/L phosphate ions can be combined with 100 mM/L calcium ions.
7 mM/L phosphate ions can be combined with 100 mM/L calcium ions.
8 mM/L phosphate ions can be combined with 100 mM/L calcium ions.
9 mM/L phosphate ions can be combined with 100 mM/L calcium ions.
9.5 mM/L phosphate ions can be combined with 100 mM/L calcium ions.
9.9 mM/L phosphate ions can be combined with 100 mM/L calcium ions.
or
1 mM/L phosphate ions can be combined with 200 mM/L calcium ions.
2 mM/L phosphate ions can be combined with 200 mM/L calcium ions.

3 mM/L phosphate ions can be combined with 200 mM/L calcium ions.
4 mM/L phosphate ions can be combined with 200 mM/L calcium ions.
5 mM/L phosphate ions can be combined with 200 mM/L calcium ions.
6 mM/L phosphate ions can be combined with 200 mM/L calcium ions.
7 mM/L phosphate ions can be combined with 200 mM/L calcium ions.
8 mM/L phosphate ions can be combined with 200 mM/L calcium ions.
9 mM/L phosphate ions can be combined with 200 mM/L calcium ions.
9.5 mM/L phosphate ions can be combined with 200 mM/L calcium ions.
9.9 mM/L phosphate ions can be combined with 200 mM/L calcium ions.
or
1 mM/L phosphate ions can be combined with 500 mM/L calcium ions.
2 mM/L phosphate ions can be combined with 500 mM/L calcium ions.
3 mM/L phosphate ions can be combined with 500 mM/L calcium ions.
4 mM/L phosphate ions can be combined with 500 mM/L calcium ions.
5 mM/L phosphate ions can be combined with 500 mM/L calcium ions.
6 mM/L phosphate ions can be combined with 500 mM/L calcium ions.
7 mM/L phosphate ions can be combined with 500 mM/L calcium ions.
8 mM/L phosphate ions can be combined with 500 mM/L calcium ions.
9 mM/L phosphate ions can be combined with 500 mM/L calcium ions.
9.5 mM/L phosphate ions can be combined with 500 mM/L calcium ions.
9.9 mM/L phosphate ions can be combined with 500 mM/L calcium ions.

In other embodiments of the invention for example and without limiting the invention the following combinations of concentrations can be used:
10 mM/L phosphate ions can be combined with 10 mM/L calcium ions.
10 mM/L phosphate ions can be combined with 15 mM/L calcium ions.
10 mM/L phosphate ions can be combined with 20 mM/L calcium ions.
10 mM/L phosphate ions can be combined with 25 mM/L calcium ions.
10 mM/L phosphate ions can be combined with 30 mM/L calcium ions.
10 mM/L phosphate ions can be combined with 35 mM/L calcium ions.
10 mM/L phosphate ions can be combined with 40 mM/L calcium ions.
10 mM/L phosphate ions can be combined with 45 mM/L calcium ions.
10 mM/L phosphate ions can be combined with 50 mM/L calcium ions.
10 mM/L phosphate ions can be combined with 60 mM/L calcium ions.
10 mM/L phosphate ions can be combined with 70 mM/L calcium ions.
10 mM/L phosphate ions can be combined with 80 mM/L calcium ions.
10 mM/L phosphate ions can be combined with 90 mM/L calcium ions.
10 mM/L phosphate ions can be combined with 100 mM/L calcium ions.
10 mM/L phosphate ions can be combined with 125 mM/L calcium ions.
10 mM/L phosphate ions can be combined with 150 mM/L calcium ions.
10 mM/L phosphate ions can be combined with 175 mM/L calcium ions.
10 mM/L phosphate ions can be combined with 200 mM/L calcium ions.
10 mM/L phosphate ions can be combined with 300 mM/L calcium ions.
10 mM/L phosphate ions can be combined with 400 mM/L calcium ions.
10 mM/L phosphate ions can be combined with 500 mM/L calcium ions.
or
15 mM/L phosphate ions can be combined with 10 mM/L calcium ions.
15 mM/L phosphate ions can be combined with 15 mM/L calcium ions.
15 mM/L phosphate ions can be combined with 20 mM/L calcium ions.
15 mM/L phosphate ions can be combined with 25 mM/L calcium ions.
15 mM/L phosphate ions can be combined with 30 mM/L calcium ions.
15 mM/L phosphate ions can be combined with 35 mM/L calcium ions.
15 mM/L phosphate ions can be combined with 40 mM/L calcium ions.
15 mM/L phosphate ions can be combined with 45 mM/L calcium ions.
15 mM/L phosphate ions can be combined with 50 mM/L calcium ions.
15 mM/L phosphate ions can be combined with 60 mM/L calcium ions.
15 mM/L phosphate ions can be combined with 70 mM/L calcium ions.
15 mM/L phosphate ions can be combined with 80 mM/L calcium ions.
15 mM/L phosphate ions can be combined with 90 mM/L calcium ions.
15 mM/L phosphate ions can be combined with 100 mM/L calcium ions.
15 mM/L phosphate ions can be combined with 125 mM/L calcium ions.
15 mM/L phosphate ions can be combined with 150 mM/L calcium ions.
15 mM/L phosphate ions can be combined with 175 mM/L calcium ions.
15 mM/L phosphate ions can be combined with 200 mM/L calcium ions.
15 mM/L phosphate ions can be combined with 300 mM/L calcium ions.
15 mM/L phosphate ions can be combined with 400 mM/L calcium ions.
15 mM/L phosphate ions can be combined with 500 mM/L calcium ions.
or
20 mM/L phosphate ions can be combined with 10 mM/L calcium ions.

20 mM/L phosphate ions can be combined with 15 mM/L calcium ions.
20 mM/L phosphate ions can be combined with 20 mM/L calcium ions.
20 mM/L phosphate ions can be combined with 25 mM/L calcium ions.
20 mM/L phosphate ions can be combined with 30 mM/L calcium ions.
20 mM/L phosphate ions can be combined with 35 mM/L calcium ions.
20 mM/L phosphate ions can be combined with 40 mM/L calcium ions.
20 mM/L phosphate ions can be combined with 45 mM/L calcium ions.
20 mM/L phosphate ions can be combined with 50 mM/L calcium ions.
20 mM/L phosphate ions can be combined with 60 mM/L calcium ions.
20 mM/L phosphate ions can be combined with 70 mM/L calcium ions.
20 mM/L phosphate ions can be combined with 80 mM/L calcium ions.
20 mM/L phosphate ions can be combined with 90 mM/L calcium ions.
20 mM/L phosphate ions can be combined with 100 mM/L calcium ions.
20 mM/L phosphate ions can be combined with 125 mM/L calcium ions.
20 mM/L phosphate ions can be combined with 150 mM/L calcium ions.
20 mM/L phosphate ions can be combined with 175 mM/L calcium ions.
20 mM/L phosphate ions can be combined with 200 mM/L calcium ions.
20 mM/L phosphate ions can be combined with 300 mM/L calcium ions.
20 mM/L phosphate ions can be combined with 400 mM/L calcium ions.
20 mM/L phosphate ions can be combined with 500 mM/L calcium ions.
or
25 mM/L phosphate ions can be combined with 10 mM/L calcium ions.
25 mM/L phosphate ions can be combined with 15 mM/L calcium ions.
25 mM/L phosphate ions can be combined with 20 mM/L calcium ions.
25 mM/L phosphate ions can be combined with 25 mM/L calcium ions.
25 mM/L phosphate ions can be combined with 30 mM/L calcium ions.
25 mM/L phosphate ions can be combined with 35 mM/L calcium ions.
25 mM/L phosphate ions can be combined with 40 mM/L calcium ions.
25 mM/L phosphate ions can be combined with 45 mM/L calcium ions.
25 mM/L phosphate ions can be combined with 50 mM/L calcium ions.
25 mM/L phosphate ions can be combined with 60 mM/L calcium ions.
25 mM/L phosphate ions can be combined with 70 mM/L calcium ions.
25 mM/L phosphate ions can be combined with 80 mM/L calcium ions.
25 mM/L phosphate ions can be combined with 90 mM/L calcium ions.
25 mM/L phosphate ions can be combined with 100 mM/L calcium ions.
25 mM/L phosphate ions can be combined with 125 mM/L calcium ions.
25 mM/L phosphate ions can be combined with 150 mM/L calcium ions.
25 mM/L phosphate ions can be combined with 175 mM/L calcium ions.
25 mM/L phosphate ions can be combined with 200 mM/L calcium ions.
25 mM/L phosphate ions can be combined with 300 mM/L calcium ions.
25 mM/L phosphate ions can be combined with 400 mM/L calcium ions.
25 mM/L phosphate ions can be combined with 500 mM/L calcium ions.
or
30 mM/L phosphate ions can be combined with 10 mM/L calcium ions.
30 mM/L phosphate ions can be combined with 15 mM/L calcium ions.
30 mM/L phosphate ions can be combined with 20 mM/L calcium ions.
30 mM/L phosphate ions can be combined with 25 mM/L calcium ions.
30 mM/L phosphate ions can be combined with 30 mM/L calcium ions.
30 mM/L phosphate ions can be combined with 35 mM/L calcium ions.
30 mM/L phosphate ions can be combined with 40 mM/L calcium ions.
30 mM/L phosphate ions can be combined with 45 mM/L calcium ions.
30 mM/L phosphate ions can be combined with 50 mM/L calcium ions.
30 mM/L phosphate ions can be combined with 60 mM/L calcium ions.
30 mM/L phosphate ions can be combined with 70 mM/L calcium ions.
30 mM/L phosphate ions can be combined with 80 mM/L calcium ions.
30 mM/L phosphate ions can be combined with 90 mM/L calcium ions.
30 mM/L phosphate ions can be combined with 100 mM/L calcium ions.
30 mM/L phosphate ions can be combined with 125 mM/L calcium ions.
30 mM/L phosphate ions can be combined with 150 mM/L calcium ions.
30 mM/L phosphate ions can be combined with 175 mM/L calcium ions.
30 mM/L phosphate ions can be combined with 200 mM/L calcium ions.
30 mM/L phosphate ions can be combined with 300 mM/L calcium ions.
30 mM/L phosphate ions can be combined with 400 mM/L calcium ions.
30 mM/L phosphate ions can be combined with 500 mM/L calcium ions.
or
40 mM/L phosphate ions can be combined with 10 mM/L calcium ions.
40 mM/L phosphate ions can be combined with 15 mM/L calcium ions.
40 mM/L phosphate ions can be combined with 20 mM/L calcium ions.

40 mM/L phosphate ions can be combined with 25 mM/L calcium ions.
40 mM/L phosphate ions can be combined with 30 mM/L calcium ions.
40 mM/L phosphate ions can be combined with 35 mM/L calcium ions.
40 mM/L phosphate ions can be combined with 40 mM/L calcium ions.
40 mM/L phosphate ions can be combined with 45 mM/L calcium ions.
40 mM/L phosphate ions can be combined with 50 mM/L calcium ions.
40 mM/L phosphate ions can be combined with 60 mM/L calcium ions.
40 mM/L phosphate ions can be combined with 70 mM/L calcium ions.
40 mM/L phosphate ions can be combined with 80 mM/L calcium ions.
40 mM/L phosphate ions can be combined with 90 mM/L calcium ions.
40 mM/L phosphate ions can be combined with 100 mM/L calcium ions.
40 mM/L phosphate ions can be combined with 125 mM/L calcium ions.
40 mM/L phosphate ions can be combined with 150 mM/L calcium ions.
40 mM/L phosphate ions can be combined with 175 mM/L calcium ions.
40 mM/L phosphate ions can be combined with 200 mM/L calcium ions.
40 mM/L phosphate ions can be combined with 300 mM/L calcium ions.
40 mM/L phosphate ions can be combined with 400 mM/L calcium ions.
40 mM/L phosphate ions can be combined with 500 mM/L calcium ions.
or
50 mM/L phosphate ions can be combined with 10 mM/L calcium ions.
50 mM/L phosphate ions can be combined with 15 mM/L calcium ions.
50 mM/L phosphate ions can be combined with 20 mM/L calcium ions.
50 mM/L phosphate ions can be combined with 25 mM/L calcium ions.
50 mM/L phosphate ions can be combined with 30 mM/L calcium ions.
50 mM/L phosphate ions can be combined with 35 mM/L calcium ions.
50 mM/L phosphate ions can be combined with 40 mM/L calcium ions.
50 mM/L phosphate ions can be combined with 45 mM/L calcium ions.
50 mM/L phosphate ions can be combined with 50 mM/L calcium ions.
50 mM/L phosphate ions can be combined with 60 mM/L calcium ions.
50 mM/L phosphate ions can be combined with 70 mM/L calcium ions.
50 mM/L phosphate ions can be combined with 80 mM/L calcium ions.
50 mM/L phosphate ions can be combined with 90 mM/L calcium ions.
50 mM/L phosphate ions can be combined with 100 mM/L calcium ions.
50 mM/L phosphate ions can be combined with 125 mM/L calcium ions.
50 mM/L phosphate ions can be combined with 150 mM/L calcium ions.
50 mM/L phosphate ions can be combined with 175 mM/L calcium ions.
50 mM/L phosphate ions can be combined with 200 mM/L calcium ions.
50 mM/L phosphate ions can be combined with 300 mM/L calcium ions.
50 mM/L phosphate ions can be combined with 400 mM/L calcium ions.
50 mM/L phosphate ions can be combined with 500 mM/L calcium ions.

The concentration of the calcium complexing agent used in step (c) is less critical. Preferably the range is above 80 mM, or above 100 mM, or above 120 mM, or above 150 mM or above 200 mM or above 250 mM or up to the upper solubility limit of the calcium complexing agent.

The man skilled in the art will optimize the desired calcium complexing agent according to the amount of calcium phosphate precipitate comprising VWF formed and will increase the concentration until the calcium complexing agent is concentrated enough to dissolve more or less completely the calcium phosphate precipitate comprising the VWF. The only upper limit is the solubility of the calcium complexing agent at the given temperature of the solution.

The temperature and the pH at which the precipitation is done is not critical. For example the temperature may be between 21° C. to 37° C. and the pH between 5.3 and 7.5.

"VWF" or "von Willebrand Factor" are used interchangeably in the present invention. The term as used herein also includes natural allelic variations that may exist and occur from one individual to another. "VWF" or "von Willebrand Factor" within the above definition further includes variants of VWF. Such variants may differ in one or more amino acid residues from the wild-type sequence. Examples of such differences may include as conservative amino acid substitutions, i.e. substitutions within groups of amino acids with similar characteristics, e.g. (1) small amino acids, (2) acidic amino acids, (3) polar amino acids, (4) basic amino acids, (5) hydrophobic amino acids, and (6) aromatic amino acids. Examples of such conservative substitutions are shown in the following table. VWF variants include also fusion proteins with VWF, for example fusion proteins with albumin or fusions to antibody fragments including fusions to the Fc part, or fusions with XTEN. Also encompassed are VWF chemically conjugated with other molecules like albumin-binding peptides, PEG, HES and other half-life enhancing conjugates. Also encompassed are any of the above VWF in a complex with FVIII, be it a non-covalent complex or a covalent linkage to FVIII.

TABLE 1

| | | | | |
|---|---|---|---|---|
| (1) | Alanine | Glycine | | |
| (2) | Aspartic acid | Glutamic acid | | |
| (3) | Asparagine | Glutamine | Serine | Threonine |
| (4) | Arginine | Histidine | Lysine | |
| (5) | Isoleucine | Leucine | Methionine | Valine |
| (6) | Phenylalanine | Tyrosine | Tryptophane | |

An additional potential benefit of those embodiments of the present invention is that the biological activity of VWF is retained.

The "Biological Activity" of wild-type VWF can be determined by the artisan using methods for ristocetin co-factor activity (VWF:RCo, Federici A B et al. 2004. Haematologica 89:77-85), binding of VWF to GP Ibα of the platelet glycoprotein complex Ib-V-IX (Sucker et al. 2006. Clin Appl Thromb Hemost. 12:305-310), or a collagen binding assay (Kallas & Talpsep. 2001. Annals of Hematology 80:466-471).

The ratio of the biological activity of VWF over the antigen content of VWF (VWF:RCo/VNWF:Ag) which is obtained according to the invention is at least 70%, preferably at least 75%, preferably at least 80%, preferably at least 85%, preferably at least 90%, preferably at least 98%, more preferable at least 98% of the corresponding ratio of the starting material, i.e. in the aqueous solution used in step (a) of the claimed method. In plasma the VWF:RCo/VWF:Ag ratio is 1.0, however recombinant VWF may also have values of 1.2 in the starting material.

The yield of VWF:RCo according to the method of the invention is at least 50%, preferably at least 60%, preferably at least 70%, preferably at least 75%, preferably at least 80%, preferably at least 85%, preferably at least 90%, most preferably at least 95%. "Separating the precipitate" in the sense of the invention is any means of separating the precipitate from the precipitation solution i.e. the aqueous solution used in step (a) of the claimed method, encompassing for example the use of separators or the use of centrifuges. If a centrifugation step is used, the supernatant is removed and the remaining precipitate is mixed with an aqueous solution comprising a calcium complexing agent.

The aqueous solution used in step (c) which comprises the calcium complexing agent is preferably a buffer, i.e. an aqueous solution comprising one or more buffering agents maintaining the pH at a certain level.

In the sense of the present invention the term "calcium complexing agent" means an agent with the ability to form a complex between calcium and the complexing agent. The formation of a complex encompasses the formation of two or more separate bindings between a polydentate ligand, i.e. the chemical compound or the polypeptide of interest and a single central atom. Usually such chemical compounds are organic chemical compounds, and are called chelants, chelators, chelating agents, or sequestering agents. The chemical compound forms a chelate complex with the single central calcium ion. Chelate complexes are contrasted with coordination complexes with monodentate ligands, which form only one bond with a central calcium. By way of non-limiting examples the following agents are chemical compounds with the ability to complex calcium according to the invention:

a) chemical compounds comprising a penta-acetic group and their various salts, like diethylene triamine pentaacetic acid (DTPA or pentetic acid), Pentetide, Ino-1 and Fura-2;
b) chemical compounds comprising a tetra-acetic group and their various salts, like 1,2-bis(o-ethane-N,N,N',N'-tetraacetic acid (BAPTA), ethylene diamine tetra-acetic acid (EDTA) and its various salts (like diammonium EDTA, dipotassium EDTA dihydrate; disodium EDTA; trisodium EDTA; tetrasodium EDTA and tetraammonium EDTA) and ethylene glycol tetra-acetic acid (EGTA);
c) chemical compounds comprising a tri-acetic group and their various salts, like N-(Hydroxyethyl) ethylene diamine tri-acetic acid (HEDTA) and nitrilotriacetic acid (NTA);
c) chemical compounds comprising a tri-acetic group and their various salts, like N-(Hydroxyethyl) ethylene diamine tri-acetic acid (HEDTA) and nitrilotriacetic (NTA);
d) chemical compounds comprising a di-acetic group and their various salts like Imino diacetic acid (IDA), tetrasodium iminodisuccinate, trisodiumcitrate and
e) chemical compounds comprising multiple amine groups, like aminoethyl-ethanolamine (AEEA), 2,3-diphenylethylenediamine, ethylen-diamine, ethylenediamine-N,N'-bis(2-hydroxyphenylacetic acid) ethylene-diamine-N,N'-disuccinic acid, tetrahydroxypropyl ethylenediamine, triethylenetetramine and polyaminocarboxylic acid
f) chemical compounds comprising multiple thiol groups, like dimeracprol, dimercaptosuccinic acid (DMSA), dimercapto-1-propanesulfonic acid (DMPS), sodium diethyldithiocarbamate
g) phosponic acid and derivatives thereof and their various salts, like aminotris(methylenephosphonic acid) (ATMP), diethylenetriamine penta(methylene phosphonic acid), ethylenediamine tetra(methylene phosphonic acid (EDTMP), etidronic acid or 1-hydroxyethane 1,1-diphosphonic acid (HEDP).

It is to be understood that listing a certain calcium complexing agent as an ion or a certain salt encompasses the ion in different salts as well.

Also the following complexing agents are chemical compounds with the ability to complex calcium in the sense of the invention. Acetylacetonic acid, Acetylacetone, Benzotriazole, 2,2'-Bipyridine, 4,4'-Bipyridine, 1,2-Bis(dimethylarsino)benzene 1,2 Bis(dimethyl-phosphino)ethane, 1,2-Bis(diphenylphosphino)-ethane, Benzotriazoles, Clathrochelate, 2.2.2-Cryptand, Catechol, Corrole, Crown ether, 18-Crown-6, Cryptand, Cyclen, Cyclodextrins, Deferasirox, Deferiprone, Deferoxamine, Dexrazoxane, Diglyme, Dimethylglyoxime, Dithiolene, Ethandiol, Etidronic acid, Ferrichrome, Gluconic acid, Metallacrown, Hydrolyzed casein, Hexafluoroacetylacetone, Penicillamine, Phenanthroline, Phosphonate, Phytochelatin, Porphin, Porphyrin, Pyrophosphate, Scorpionate ligand, Sodium poly(aspartate), Terpyridine, Tetraphenyl-porphyrin, 1,4,7-Triazacydononane, Trimetaphosphates Triphos, and 1,4,7-Trithiacyclononane.

An especially preferred embodiment of the invention are processes using ethylene diamine tetraacetic acid (EDTA) as the calcium complexing agent in the sense of the invention. EDTA is a polyamino carboxylic acid with the formula [CH2N(CH2CO2H)2]2. Its usefulness arises because of its role as a chelating agent, i.e. its ability to "sequester" metal ions such as $Ca^{2+}$ and $Fe^{3+}$. After being bound by EDTA, metal ions remain in solution but exhibit diminished reactivity. EDTA is produced as several salts, notably disodium EDTA and calcium disodium EDTA. The molecular weight is 292.24 Da. In coordination chemistry, $EDTA^{4-}$ is a member of the polyamino carboxylic acid family of ligands. $EDTA^{4-}$ usually binds to a metal cation through its two amines and four carboxylates. Many of the resulting coordination chemical compounds adopt octahedral geometry. EDTA is also capable to bind to cationic charges of AEX matrices.

Also especially preferred embodiments of the invention are processes using Ethylene glycol tetra-acetic acid (EGTA) as the chemical compound.

The VWF, VWF proteins or a complex of VWF and Factor VIII as described in this invention can be formulated into pharmaceutical preparations for therapeutic use. The purified protein or proteins may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3rd edition, Kibbe et al., Pharmaceutical Press (2000)). In particular, the pharmaceutical composition comprising the polypeptide variant of the invention may be formulated in lyophilized or stable liquid form. The polypeptide variant may be lyophilized by a variety of procedures known in the art. Lyophilized formulations are reconstituted prior to use by the addition of one or more pharmaceutically acceptable diluents such as sterile water for injection or sterile physiological saline solution.

Formulations of the composition are delivered to the individual by any pharmaceutically suitable means of administration. Various delivery systems are known and can be used to administer the composition by any convenient route. Preferentially, the compositions of the invention are administered systemically. For systemic use, insertion proteins of the invention are formulated for parenteral (e.g. intravenous, subcutaneous, intramuscular, intraperitoneal, intracerebral, intrapulmonar, intranasal or transdermal) or enteral (e.g., oral, vaginal or rectal) delivery according to conventional methods. The most preferential routes of administration are intravenous and subcutaneous administration. The formulations can be administered continuously by infusion or by bolus injection. Some formulations encompass slow release systems.

The pharmaceutical preparations prepared by the invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The pharmaceutical composition prepared by the method of the invention may be administered alone or in conjunction with other therapeutic agents. These agents may be incorporated as part of the same pharmaceutical. One example of such an agent is the combination of modified Factor VIII with non-modified VWF or the combination of non-modified Factor VIII with modified VWF or the combination of modified Factor VIII with modified VWF.

EXAMPLES

All samples were tested using the Behring Coagulation Timer (BCT) and the Siemens Healthcare Diagnostics Reagent kits for VWF:Ag (antigen) and VWF:RCo (activity). The calculated ratio of RCo/Ag is an indicator for the quality of VWF. A decrease of that value during the process would signal a loss of VWF quality meaning a loss of biological activity of the purified VWF in relation to the amount of purified VWF antigen.

The starting material for the Examples 1 to 11 was recombinant VWF albumin fusion protein as described in WO 2009/156137 in CHO cells but produced in synthetic PowerCHO-3CD medium (Lonza Cat.N. BESP1073Q). Cell culture supernatant was harvested from a 5 liter perfusion fermenter, which run up to 26 days with a 1.5 perfusion factor (around 10 liter supernatant per harvest was collected every second day starting at day six). The filtered harvests were aliquoted and frozen at $-80°$ C. A stock solution of 250 mM/L phosphate buffered saline (PBS) was prepared by dissolving a bag of ready to use PBS (Sigma; P-5368) in 40 mL $H_2O$. The used EDTA in all experiment was EDTA disodium dihydrate but later named only EDTA. The used $CaCl_2$ was $CaCl_2$ dihydrate.

Example 1: Precipitation of rVWF-FP from Cell Culture Supernatant Using Different Phosphate Concentrations Four preparations of a 40 mL supernatant were prepared and phosphate stock solution was added as shown in Table 2 below.

TABLE 2

| | Final phoshate concentration (mM/L) | µL |
|---|---|---|
| preparation 1 | 1.0 | 160 |
| preparation 2 | 2.5 | 400 |
| preparation 3 | 5.0 | 800 |
| preparation 4 | 7.5 | 1200 |

After mixing, 1.663 mL of a 1 mol/L $CaCl_2*2\ H_2O$ solution was added to the preparation with stirring at 30° C. to 37° C. in a water bath. Accordingly, the final concentration of calcium was about 40 mM/L. Calcium was added within two minutes with mixing and followed by an additional six minutes holding time without mixing. The resulting precipitate was separated by a 30-minute centrifugation at 3,000×g. The separated precipitate was redissolved in a buffer consisting of 20 mM/L HEPES+120 mM/L EDTA at pH 7.2 and 37° C.

The data in Table 3 show that 5 mM phosphate gave the best yield in the dissolved pellet. It seems that the whole concentration of phosphate that was tested also worked and had no negative influence on the VWF:RCo/VWF:Ag ratio

TABLE 3

|  | volume (mL) | vWF:Ag | | | vWF:Rco | | | ratio |
|  |  | conc. (IU/ml) | total (IU) | yield (%) | conc. (IU/ml) | total (IU) | yield (%) | RCo/Ag (IU/IU) |
| --- | --- | --- | --- | --- | --- | --- | --- | --- |
| inital solution | 40 | 4.5 | 180 | 100% | 4.9 | 197 | 100% | 1.09 |
| dissolved pellet 1.0 mM | 3 | 17.9 | 54 | 30% | 21.1 | 63 | 32% | 1.18 |
| dissolved pellet 2.5 mM | 3 | 37.2 | 112 | 62% | 41.9 | 126 | 64% | 1.13 |
| dissolved pellet 5.0 mM | 3 | 49.5 | 149 | 83% | 57.4 | 172 | 87% | 1.16 |
| dissolved pellet 7.5 mM | 3 | 45.9 | 138 | 77% | 46.5 | 140 | 71% | 1.01 |

Example 2: Precipitation of rVWF-FP from Cell Culture Supernatant with Different Calcium Concentrations Four preparations a 40 mL supernatant were prepared and in each case 800 μL phosphate stock solution were added leading to a phosphate concentration of 5 mM. After preparing a 1 mol/L CaCl$_2$*2 H$_2$O solution different amounts of that solution were added to the preparation with stirring at 30° C. to 37° C. in a water bath to get four different concentration as shown in Table 4.

TABLE 4

| | Final calcium concentration mM/L | mL |
| --- | --- | --- |
| preparation 1 | 20 | 0.730 |
| preparation 2 | 40 | 1,487 |
| preparation 3 | 60 | 2,280 |
| preparation 4 | 80 | 3,105 |

The addition of the calcium solution took two minutes with mixing followed by an additional six minutes holding time without mixing. The resulting precipitate was separated by a 30-minute centrifugation at 3,000×g. The separated precipitate was redissolved in a buffer consisting of 20 mM/L HEPES+120 mM/L EDTA at pH 7.2 and 37° C.

The data in Table 5 show that 60 mM CaCl$_2$+2H$_2$O gave the best yield. There is no real difference in the VWF:RCo/VWF:Ag ratio for all preparations and only a slight decrease after precipitation.

Example 3: Precipitation of rVWF-FP from Cell Culture Supernatant at Different pH Values Four preparations a 40 mL supernatant were prepared and in each case 800 μL phosphate stock solution were added leading to a phosphate concentration of 5 mM. After mixing, 1.663 mL of a 1 mol/L CaCl$_2$*2 H$_2$O solution at different pH values were added to the different supernatants bringing the solutions to about 40 mM/L calcium at the different pH values shown in Table 6 below with stirring at 30° C. to 37° C. in a water bath.

TABLE 6

| | pH |
| --- | --- |
| preparation 1 | 5.3 |
| preparation 2 | 6.5 |
| preparation 3 | 7.0 |
| preparation 4 | 7.5 |

The addition took place during two minutes with mixing followed by an additional six minutes holding time without mixing. The precipitate was separated by a 30-minute centrifugation at 3,000×g. The separated precipitate was redissolved in a buffer consisting of 20 mM/L HEPES+120 mM/L EDTA at pH 7.2 and 37° C.

The data in Table 7 show that the pH of the CaCl$_2$*2H$_2$O had no influence on the precipitation performance. The slight differences are most likely due to test variability. pH 5.3 is representing CaCl$_2$+2H$_2$O solution which was not pH adjusted and therefore pH 5.3 was kept during the following Examples.

TABLE 5

| description | volume (mL) | vWF:Ag | | | vWF:RCo | | | ratio |
|  |  | conc. (IU/ml) | total (IU) | yield (%) | conc. (IU/ml) | total (IU) | yield (%) | RCo/Ag (IU/IU) |
| --- | --- | --- | --- | --- | --- | --- | --- | --- |
| initial solution | 35 | 3.6 | 127 | 100% | 4.9 | 170 | 100% | 1.34 |
| dis. pellet 20 mM | 2.3 | 38.4 | 88 | 70% | 47.7 | 110 | 65% | 1.24 |
| dis. pellet 40 mM | 2.3 | 43.2 | 99 | 78% | 54.9 | 126 | 74% | 1.27 |
| dis. pellet 60 mM | 2.3 | 47.1 | 108 | 85% | 60.4 | 139 | 82% | 1.28 |
| dis. pellet 80 mM | 2.3 | 47.4 | 109 | 86% | 57.6 | 132 | 78% | 1.21 |

TABLE 7

| description | volume (mL) | VWF:Ag conc. (IU/ml) | VWF:Ag total (IU) | VWF:Ag yield (%) | VWF:RCo conc. (IU/ml) | VWF:RCo total (IU) | VWF:RCo yield (%) | ratio RCo/Ag (IU/IU) |
|---|---|---|---|---|---|---|---|---|
| initial solution | 40 | 4.5 | 180 | 100% | 4.9 | 197 | 100% | 1.09 |
| dissolved pellet pH 5.3 | 3 | 51.0 | 153 | 85% | 54.2 | 163 | 83% | 1.06 |
| dissolved pellet pH 6.0 | 3 | 48.3 | 145 | 81% | 52.3 | 157 | 80% | 1.08 |
| dissolved pellet pH 6.5 | 3 | 51.3 | 154 | 86% | 53.0 | 159 | 81% | 1.03 |
| dissolved pellet pH 7.0 | 3 | 52.2 | 157 | 87% | 56.8 | 170 | 87% | 1.09 |

Example 4: Precipitation of rVWF-FP from Cell Culture Supernatant and Redissolving with Buffers of Different pH Values Four preparations of a 40 mL supernatant were prepared and in each case 800 μL phosphate stock solution were added leading to a phosphate concentration of 5 mM. After mixing, 1.663 mL of a 1 mol/L $CaCl_2 \cdot 2 H_2O$-solution was added to the preparation with stirring at 30° C.-37° C. in a water bath bringing the solution to about 40 mM/L calcium. The addition took place within two minutes with mixing followed by an additional six minutes holding time without mixing. The precipitate was then separated by a 30-minute centrifugation at 3,000×g.

The separated precipitate was redissolved in a buffer consisting of 20 mM/L HEPES+120 mM/L EDTA at 37° C. and at different pH values as shown in Table 8 below.

TABLE 8

| | pH |
|---|---|
| preparation 1 | 6.4 |
| preparation 2 | 6.8 |
| preparation 3 | 7.2 |
| preparation 4 | 7.6 |

The data in Table 9 show that the pH of the solution buffer had no influence on the precipitation performance. The slight differences are most likely test due to test variability. For future experiments a pH 7.2 was chosen.

TABLE 9

| description | volume (mL) | vWF:Ag conc. (IU/ml) | vWF:Ag total (IU) | vWF:Ag yield (%) | vWF:RCo conc. (IU/ml) | vWF:RCo total (IU) | vWF:RCo yield (%) | ratio RCo/Ag (IU/IU) |
|---|---|---|---|---|---|---|---|---|
| initial solution | 40 | 4.5 | 179 | 100% | 4.5 | 178 | 100% | 0.99 |
| dissolved pellet pH 6.4 | 3 | 48.9 | 147 | 82% | 49.8 | 149 | 84% | 1.02 |
| dissolved pellet pH 6.8 | 3 | 44.1 | 132 | 74% | 42.7 | 128 | 72% | 0.97 |
| dissolved pellet pH 7.2 | 3 | 48.6 | 146 | 81% | 53.5 | 161 | 90% | 1.10 |
| dissolved pellet pH 7.6 | 3 | 51.9 | 156 | 87% | 52.1 | 156 | 88% | 1.00 |

Example 5: Precipitation of rVWF-FP from Cell Culture Supernatant and Redissolving with Different EDTA Concentration of the Solution Buffer Four preparations of a 40 mL supernatant were prepared and in each case 800 μL phosphate stock solution were added leading to a phosphate concentration of 5 mM. After mixing, 1.663 mL of a 1 mol/L $CaCl_2 \cdot 2 H_2O$-solution was added to the preparation with stirring at 30° C.-37° C. in a water bath bringing the solution to about 40 mM/L calcium. The addition took place within two minutes with mixing followed by an additional six minutes holding time without mixing. The precipitate was then separated by a 30-minute centrifugation at 3,000×g.

The separated precipitate was redissolved in a buffer consisting of 20 mM/L HEPES at a pH of 7.2 at 37° C. and at different EDTA concentrations as shown in Table 10 below.

TABLE 10

| | mM/L EDTA |
|---|---|
| preparation 1 | 80 |
| preparation 2 | 120 |
| preparation 3 | 160 |
| preparation 4 | 200 |

The data in Table 11 show that 120 mM EDTA gave the best yield, though all other concentrations tested worked almost as well. There was no real difference in the ratio between all preparations.

TABLE 11

| | vWF:Ag | | | | vWF:RCo | | | ratio |
|---|---|---|---|---|---|---|---|---|
| | volume (mL) | conc. (IU/ml) | total (IU) | yield (%) | conc. (IU/ml) | total (IU) | yield (%) | RCo/Ag (IU/IU) |
| initial solution | 40 | 4.6 | 185 | 100% | 4.5 | 178 | 100% | 0.96 |
| dissolved pellet 80 mM | 3 | 41.2 | 124 | 67% | 44.8 | 135 | 76% | 1.09 |
| dissolved pellet 120 mM | 3 | 48.3 | 145 | 78% | 52.8 | 158 | 89% | 1.09 |
| dissolved pellet 160 mM | 3 | 47.1 | 141 | 76% | 49.1 | 147 | 83% | 1.04 |
| dissolved pellet 200 mM | 3 | 46.8 | 140 | 76% | 47.0 | 141 | 79% | 1.01 |

Example 6: Precipitation of rVWF-FP from Cell Culture Supernatant at Different Temperatures Four preparations of a 40 mL supernatant were prepared and in each case 800 µL phosphate stock solution were added leading to a phosphate concentration of 5 mM. After mixing, 1.663 mL of a 1 mol/L CaCl$_2$*2 H$_2$O-solution was added to the preparation bringing the solution to about 40 mM/L calcium with stirring at four different temperatures as shown in Table 12 in a water bath.

TABLE 12

| | temperature |
|---|---|
| preparation 1 | 21° C. |
| preparation 2 | 25° C. |
| preparation 3 | 30° C. |
| preparation 4 | 37° C. |

The addition took place within two minutes with mixing followed by an additional six minutes holding time without mixing. The precipitate was then separated by a 30-minute centrifugation at 3,000×g.

The separated precipitate was redissolved in a buffer consisting of 20 mM/L HEPES and 120 mM EDTA at a pH of 7.2 at 37° C.

The data in Table 13 show that a slight increase in yield and ratio could be realized by precipitating at a temperature of 37° C.

TABLE 13

| | | VWF:Ag | | | VWF:RCo | | | ratio |
|---|---|---|---|---|---|---|---|---|
| description | volume (mL) | conc. (IU/ml) | total (IU) | yield (%) | conc. (IU/ml) | total (IU) | yield (%) | RCo/Ag (IU/IU) |
| inital solution | 40 | 4.6 | 185 | 100% | 4.8 | 190 | 100% | 1.03 |
| dissolved pellet 21° C. | 3 | 50.7 | 152 | 82% | 50.6 | 152 | 80% | 1.00 |
| dissolved pellet 25° C. | 3 | 51.6 | 155 | 84% | 51.6 | 155 | 81% | 1.00 |
| dissolved pellet 30° C. | 3 | 52.2 | 157 | 85% | 54.4 | 163 | 86% | 1.04 |
| dissolved pellet 37° C. | 3 | 52.5 | 158 | 85% | 56.3 | 169 | 89% | 1.07 |

Example 7: Precipitation of rVWF-FP from Cell Culture Supernatant with Centrifugation at Different Length Four preparations of a 35 mL supernatant were prepared and in each case 800 µL phosphate stock solution were added leading to a phosphate concentration of 5 mM.

After mixing, 1.663 mL of a 1 mol/L CaCl$_2$*2 H$_2$O-solution was added to the preparation with stirring at 37° C. in a water bath bringing the solution to about 40 mM/L calcium. The addition took place within two minutes with mixing followed by an additional six minutes holding time without mixing. The precipitate was then separated by centrifugation at 3,000×g for various time lengths as indicated in Table 14.

TABLE 14

| | centrifugation time (minutes) |
|---|---|
| preparation 1 | 10 |
| preparation 2 | 20 |
| preparation 3 | 30 |
| preparation 4 | 40 |

The isolated precipitate was redissolved in a buffer consisting of 20 mM/L HEPES and 120 mM EDTA at a pH of 7.2 at 37° C.

The data in Table 15 show that the centrifugation time has no influence on the precipitation performance. The slight differences are most likely due to test variability. A shorter centrifugation time might, however, be of interest in order to reduce the overall process time.

TABLE 15

| description | volume (mL) | VWF:Ag conc. (IU/ml) | VWF:Ag total (IU) | VWF:Ag yield (%) | VWF:RCo conc. (IU/ml) | VWF:RCo total (IU) | VWF:RCo yield (%) | ratio RCo/Ag (IU/IU) |
|---|---|---|---|---|---|---|---|---|
| initial solution | 35 | 3.6 | 127 | 100% | 5.0 | 173 | 100% | 1.36 |
| dis. pellet 10 min | 2.3 | 48.0 | 110 | 87% | 65.7 | 151 | 87% | 1.37 |
| dis. pellet 20 min | 2.3 | 48.9 | 112 | 89% | 69.3 | 159 | 92% | 1.42 |
| dis. pellet 30 min | 2.3 | 47.7 | 110 | 86% | 62.9 | 145 | 83% | 1.32 |
| dis. pellet 40 min | 2.3 | 47.4 | 109 | 86% | 61.6 | 142 | 82% | 1.30 |

Example 8: Precipitation of rVWF-FP from Cell Culture Supernatant with Different Phosphate and Redissolving the Precipitate at Different EDTA Concentrations Six preparations a 40 mL supernatant were prepared and phosphate stock solution was added to obtain final phosphate concentration as shown in Table 16.

TABLE 16

| | Final phosphate concentr. mM/L | µL |
|---|---|---|
| preparation 1 | 5.0 | 800 |
| preparation 2 | 5.0 | 800 |
| preparation 3 | 7.5 | 1200 |
| preparation 4 | 7.5 | 1200 |
| preparation 5 | 10 | 1600 |
| preparation 6 | 10 | 1600 |

After mixing, 1.663 mL of a 1 mol/L $CaCl_2 \cdot 2H_2O$-solution was added to the preparation with stirring at 37° C. in a water bath bringing the solution to about 40 mM/L calcium. The addition took place within two minutes with mixing followed by an additional six minutes holding time without mixing.

The isolated precipitates of preparations 1/3/5 were redissolved at 37° C. in a 20 mM/L HEPES+120 mM/L EDTA-buffer at pH 7.2 and preparations 2/4/6 were redissolved at 37° C. in 20 mM/L HEPES+160 mM/L EDTA-buffer pH7.2.

The data in Table 17 show that 5 mM phosphate gives the best yield with both EDTA concentrations in dissolve pellet. The yields of the other buffer combination are decreasing, though do still give satisfying yields.

Example 9: Precipitation of rVWF-FP from Cell Culture Supernatant and Solving with Buffer Containing EGTA 800 µL phosphate stock solution was added to 40 mL supernatant bringing the solution to 5 mM phosphate. After mixing, 1.663 mL 1 mol/L CaCl2+2H2O-solution was added to the preparation with stirring at 37° C. in a water bath bringing the solution to about 40 mM/L CaCl2+2H2O. The addition took place for two minutes with mixing followed by an additional six minutes holding time without mixing. The precipitate was isolated by a 30-minute centrifugation at 3,000×g. The isolated precipitate was redissolved at 37° C. with a buffer consisting of 20 mM/L HEPES and 120 mM/L EGTA at pH 7.2.

The data in Table 18 show that EGTA may be used instead of EDTA for redissolving the pellet with comparable yield.

TABLE 17

| description | volume (mL) | VWF:Ag conc. (IU/ml) | VWF:Ag total (IU) | VWF:Ag yield (%) | VWF:RCo conc. (IU/ml) | VWF:RCo total (IU) | VWF:RCo yield (%) | ratio RCo/Ag (IU/IU) |
|---|---|---|---|---|---|---|---|---|
| initial solution | 40 | 4.4 | 176 | 100% | 4.8 | 193 | 100% | 1.10 |
| dis. pellet 5.0/120 mM | 3 | 54.0 | 162 | 92% | 55.4 | 166 | 86% | 1.03 |
| dis. pellet 5.0/160 mM | 3 | 54.0 | 162 | 92% | 56.6 | 170 | 88% | 1.05 |
| dis. pellet 7.5/120 mM | 3 | 43.2 | 130 | 74% | 46.9 | 141 | 73% | 1.09 |
| dis. pellet 7.5/160 mM | 3 | 48.0 | 144 | 82% | 52.1 | 156 | 81% | 1.09 |
| dis. pellet 10/120 mM | 3 | 36.0 | 108 | 61% | 36.3 | 109 | 56% | 1.01 |
| dis. pellet 10/160 mM | 3 | 41.7 | 125 | 71% | 48.8 | 147 | 76% | 1.17 |

TABLE 18

| description | VWF:Ag | | | | VWF:RCo | | | ratio |
| --- | --- | --- | --- | --- | --- | --- | --- | --- |
| | volume (mL) | conc. (IU/ml) | total (IU) | yield (%) | conc. (IU/ml) | total (IU) | yield (%) | RCo/Ag (IU/IU) |
| initial solution | 40 | 3.9 | 156 | 100% | 3.8 | 152 | 100% | 0.98 |
| dis. pellet | 3 | 36.0 | 108 | 69% | 40.2 | 121 | 79% | 1.12 |

Example 10: Precipitation of rVWF-FP from Cell Culture Supernatant with Different Phosphate, Calcium Concentration and Redissolving the Precipitate at Different EDTA Concentrations This example should evaluate if 4 or 10 time increased concentration of the three buffer components still works and if 4 or 10 time increase of the phosphate concentration alone has some impact on the precipitation. As control the standard concentration were tested too (preparation 1).

Five preparations a 35 mL supernatant were prepared and phosphate stock solution was added to obtain final phosphate concentration as shown in Table 19. Different amounts of a 1 mol/L $CaCl_2 * 2\ H_2O$ of that solution as shown in Table 19 were added to the preparation with stirring at 37° C. in a water bath. The addition took place within two minutes with mixing followed by an additional six minutes holding time without mixing. The precipitate was isolated by a 30-minute centrifugation at 3,000×g. The isolated precipitate was redissolved at 37° C. with a buffer consisting of 20 mM/L HEPES and different concentration of EDTA as shown in Table 19 at pH 7.2.

TABLE 19

| | Phosphate mM/L | Calcium mM/L | EDTA mM/L |
| --- | --- | --- | --- |
| preparation 1 | 5 | 50 | 120 |
| preparation 2 | 20 | 200 | 480 |
| preparation 3 | 50 | 500 | 667 |

The data in Table 20 show that a 4 time increase of buffer concentration (Preparation 2) still gives good results but the 10 time increase (preparation 3) didn't work because of the fact that the 667 mM EDTA (instead of the wanted 1200 mM) is the upper solubility limit and it seems that the amount is not high enough to get the pellet solved. Only increasing the phosphate concentration for 4 or 10 time didn't work. The precipitation did work what is shown by the increased pellet weight but redissolving did not work. The standard concentration of preparation 1 was giving the expected good results.

TABLE 20

| description | vWF:Ag | | | | vWF:RCo | | | ratio | pellet |
| --- | --- | --- | --- | --- | --- | --- | --- | --- | --- |
| | volume (mL) | conc. (IU/ml) | total (IU) | yield (%) | conc. (IU/ml) | total (IU) | yield (%) | RCo/Ag (IU/IU) | weight gram |
| initial solution | 35 | 0.71 | 25 | 100% | 0.85 | 30 | 100% | 1.20 | |
| dissolved pellet 1 5/50/120 | 3.5 | 7.7 | 27 | 108% | 7.7 | 27 | 91% | 1.00 | 0.43 |
| dissolved pellet 2 20/200/480 | 6.0 | 4.1 | 25 | 100% | 4.2 | 25 | 85% | 1.02 | 2.95 |
| dissolved pellet 3 50/500/667 | 6.0 | 0.47 | 3 | 11% | <0.099 | | | | 3.85 |

Example 11: Precipitation of rVWF-FP from Cell Culture Supernatant with Different Phosphate, Calcium Concentration and Redissolving the Precipitate at Different EDTA Concentrations This example evaluated whether 4 or 10 time increased concentrations of calcium or EDTA alone still works and whether 1/5 decreased concentration of the three buffer components still works. As control the standard concentration were tested too (preparation 1).

Six preparations a 35 mL supernatant were prepared and phosphate stock solution was added to obtain final phosphate concentration as shown in Table 21. Different amounts of a 1 mol/L $CaCl_2 * 2\ H_2O$ solution as shown in Table 21 were added to the preparation with stirring at 37° C. in a water bath. The addition took place within two minutes with mixing followed by an additional six minutes holding time without mixing. The precipitate was isolated by a 30-minute centrifugation at 3,000×g. The isolated precipitate was redissolved at 37° C. with a buffer consisting of 20 mM/L HEPES and different concentration of EDTA as shown in Table 21 at pH 7.2.

TABLE 21

| | Phosphate mM/L | Calcium mM/L | EDTA mM/L |
| --- | --- | --- | --- |
| preparation 1 | 5 | 50 | 120 |
| preparation 2 | 5 | 200 | 120 |
| preparation 3 | 5 | 500 | 120 |
| preparation 4 | 5 | 50 | 667 |
| preparation 5 | 5 | 50 | 120 |
| preparation 6 | 1 | 10 | 24 |

The data in Table 22 show that increasing the calcium concentration 4 and 10 time has mostly no impact on the pellet size but the yield is clearly decreased depending on the calcium concentration. Only increasing the EDTA concentration for 4 or 10 time worked very well. The yield was the same as with the standard concentration but the quality was getting better. Unfortunately a high EDTA concentration resulting in high conductivity is not preferable for the dissolved pellet so that these high EDTA concentrations are less preferred. Decreasing the salt concentration 1/5 time did not work. There was mostly all material in the supernatant of preparation 6 and the pellet was very small. The standard concentration of preparation 1 was giving the expected good results.

TABLE 22

| description | volume (mL) | vWF:Ag | | | vWF:RCo | | | ratio | pellet |
| | | conc. (IU/ml) | total (IU) | yield (%) | conc. (IU/ml) | total (IU) | yield (%) | RCo/Ag (IU/IU) | weight gram |
|---|---|---|---|---|---|---|---|---|---|
| inital solution | 35 | 1.87 | 65 | 100% | 2.17 | 76 | 100% | 1.16 | |
| supernate 1 5/50/120 | 37 | <0.09 | | | | | | | |
| supernate 2 5/200/120 | 44 | <0.09 | | | | | | | |
| supernate 3 5/500/120 | 70 | <0.09 | | | | | | | |
| supernate 4 5/50/480 | 37 | <0.09 | | | | | | | |
| supernate 5 5/50/667 | 37 | <0.09 | | | | | | | |
| supernate 6 1/10/24 | 36 | 1.66 | 59 | 90% | | | | | |
| dissolved pellet 1 | 2.7 | 24.0 | 64 | 97% | 22.9 | 61 | 80% | 0.95 | 0.50 |
| dissolved pellet 2 | 2.5 | 18.6 | 47 | 71% | 18.0 | 45 | 59% | 0.97 | 0.52 |
| dissolved pellet 3 | 2.3 | 13.8 | 32 | 49% | 11.4 | 26 | 35% | 0.83 | 0.53 |
| dissolved pellet 4 | 2.6 | 24.6 | 64 | 98% | 25.0 | 65 | 86% | 1.02 | 0.43 |
| dissolved pellet 5 | 2.6 | 24.4 | 63 | 97% | 25.1 | 65 | 86% | 1.03 | 0.43 |
| dissolved pellet 6 | 2.4 | 2.7 | 6 | 10% | 2.8 | 7 | 9% | 1.04 | 0.08 |

Example 12: Precipitation of rVWF-FP from Cell Culture Supernatant with Different Phosphate, Calcium Concentration and Redissolving the Precipitate at Different EDTA Concentrations This example evaluated whether increasing concentrations of phosphate and calcium with the same ratio of 1:1 still works. The EDTA concentration was only increased to make sure that the precipitate could get resolved. As control the standard concentration were tested too (preparation 1).

Six preparations a 30 mL supernatant were prepared and phosphate stock solution was added to obtain final phosphate concentration as shown in Table 23. Different amounts of a 1 mol/L CaCl$_2$*2 H$_2$O solution as shown in Table 23 were added to the preparation with stirring at 37° C. in a water bath. The addition took place within two minutes with mixing followed by an additional six minutes holding time without mixing. The precipitate was isolated by a 30-minute centrifugation at 3,000×g. The isolated precipitate was redissolved at 37° C. with a buffer consisting of 20 mM/L HEPES and different concentration of EDTA as shown in Table 23 at pH 7.2.

TABLE 23

| | Phosphate mM/L | Calcium mM/L | EDTA mM/L |
|---|---|---|---|
| preparation 1 | 5 | 50 | 120 |
| preparation 2 | 2 | 2 | 120 |
| preparation 3 | 5 | 5 | 120 |
| preparation 4 | 10 | 10 | 480 |
| preparation 5 | 25 | 25 | 667 |
| preparation 6 | 50 | 50 | 667 |

The data in Table 24 show that increasing the phosphate and calcium concentration 5 (preparation 5) or 10 (preparation 6) times the standard phosphate concentration, the yield is comparable to the standard preparation but the precipitate pellet size is significant increased. Preparation 4 with twice the amount of phosphate gives a slightly decrease yield, but the precipitate pellet is nearly double the size of the standard preparation. Preparation 2 and 3 ended up having mostly all VWF still in the supernatant and therefore a very unsatisfying yield. The standard concentration of preparation 1 was giving the expected good results.

TABLE 24

| description | volume (mL) | vWF:Ag | | | vWF:RCo | | | ratio | pellet |
| | | conc. (IU/ml) | total (IU) | yield (%) | conc. (IU/ml) | total (IU) | yield (%) | RCo/Ag (IU/IU) | weight gram |
|---|---|---|---|---|---|---|---|---|---|
| initial solution | 30 | 3.96 | 119 | 100% | 5.58 | 167 | 100% | 1.41 | |
| supernate 1 5/50/120 | 31 | <0.09 | | | | | | | |
| supernate 2 2/2/120 | 30 | 3.52 | 104 | 87% | | | | | |
| supernate 3 5/5/120 | 30 | 3.04 | 91 | 77% | | | | | |
| supernate 4 10/10/480 | 30 | 0.59 | 18 | 15% | | | | | |
| supernate 5 25/25/667 | 30 | <0.09 | | | | | | | |
| supernate 6 50/50/667 | 30 | <0.09 | | | | | | | |
| dissolved pellet 1 | 2.4 | 44.7 | 107 | 90% | 57.2 | 137 | 82% | 1.28 | 0.42 |
| dissolved pellet 2 | 2.0 | 1.3 | 3 | 2% | 1.8 | 4 | 2% | 1.41 | 0.03 |
| dissolved pellet 3 | 2.3 | 8.4 | 19 | 16% | 9.9 | 23 | 14% | 1.18 | 0.17 |
| dissolved pellet 4 | 2.9 | 34.5 | 100 | 84% | 43.8 | 127 | 76% | 1.27 | 0.90 |
| dissolved pellet 5 | 4.6 | 24.6 | 113 | 95% | 29.9 | 138 | 82% | 1.22 | 2.80 |
| dissolved pellet 6 | 4.9 | 23.0 | 112 | 95% | 28.8 | 141 | 84% | 1.25 | 3.18 |

Example 13: Precipitation of rVWF-FP from Cell Culture Supernatant with Fix Low Phosphate, Different Calcium Concentrations and Redissolving the Precipitate with 120 mM EDTA This example evaluated whether increasing concentrations of calcium by low constant phosphate concentration can work. As control the standard concentration were tested too (preparation 1).

Six preparations a 30 mL supernatant were prepared and phosphate stock solution was added to obtain final phosphate concentration of 2 mM/L. Different amounts of a 1 mol/L $CaCl_2*2 H_2O$ solution as shown in Table 25 were added to the preparation with stirring at 37° C. in a water bath. The addition took place within two minutes with mixing followed by an additional six minutes holding time without mixing. The precipitate was isolated by a 30-minute centrifugation at 3,000×g. The isolated precipitate was redissolved at 37° C. with a buffer consisting of 20 mM/L HEPES and 120 mM/L EDTA as shown in Table 25 at pH 7.2.

TABLE 25

| | Phosphate mM/L | Calcium mM/L | EDTA mM/L |
|---|---|---|---|
| preparation 1 | 5 | 50 | 120 |
| preparation 2 | 2 | 2 | 120 |
| preparation 3 | 2 | 4 | 120 |
| preparation 4 | 2 | 8 | 120 |
| preparation 5 | 2 | 16 | 120 |
| preparation 6 | 2 | 32 | 120 |

The data in Table 26 show that increasing the calcium concentration by doubling the calcium concentration every following experiment can end up in a good yield comparable with the standard preparation (Preparation 6, 32 mM/L calcium) even with a low phosphate concentration which is not working with a 1:1 ratio to the calcium concentration (As in Example 12 too). Low calcium concentration, lower than 16 mM/L as in preparation 2, 3 and 4 containing mostly all VWF in the supernatant and the pellet size is very small. Preparation 5 with 16 mM/L calcium gives an acceptable yield which is much lower than the standard preparation. The standard concentration of preparation 1 was giving the expected good results.

Example 14: Precipitation of rVWF-FP from Supernatant at a Larger Scale

Recombinant von-Willebrand-factor albumin fusion protein was produced in phosphate-containing, synthetic CD-CHO-medium with CHO-cells as described in WO 2009/156137.

The phosphate concentration was estimated to be about 4 mM/L. 440 mL of a 1 mol/L $CaCl_2+2H_2O$-solution was added to 10,500 mL cell-free supernatant with stirring at 25° C.-30° C. in a water bath. Accordingly, the final calcium concentration was about 40 mM/L. The addition took place within two minutes with mixing followed by an additional six minutes holding time without mixing. The precipitate was separated by a 30-minute centrifugation at 3,000×g.

The separated precipitate was redissolved at 37° C. in a buffer consisting of 20 mM/L HEPES+100 mM/L EDTA. The resulting solution of 800 mL was diluted with a 10 mM//L HEPES+3 mM/L EDTA-solution to get to a conductivity of 8 mS/cm for subsequent chromatography.

Surprisingly the results in Table 27 are showing that the yield of that purification are very high with 96% in both antigen and activity and keeps the VWF:RCo/VWF:Ag ratio during precipitation. The final rVWF-FP has still very good quality.

TABLE 26

| description | volume (mL) | vWF:Ag conc. (IU/ml) | vWF:Ag total (IU) | vWF:Ag yield (%) | vWF:RCo conc. (IU/ml) | vWF:RCo total (IU) | vWF:RCo yield (%) | ratio RCo/Ag (IU/IU) | pellet weight gram |
|---|---|---|---|---|---|---|---|---|---|
| inital solution | 30 | 3.87 | 116 | 100% | 5.61 | 168 | 100% | 1.45 | |
| supernate 1 5/50/120 | 32 | <0.09 | | | | | | | |
| supernate 2 2/2/120 | 31 | 3.70 | 115 | 99% | | | | | |
| supernate 3 2/4/120 | 30 | 3.60 | 108 | 93% | | | | | |
| supernate 4 2/8/120 | 30 | 3.03 | 91 | 78% | | | | | |
| supernate 5 2/16/120 | 31 | 1.51 | 47 | 40% | | | | | |
| supernate 6 2/32/120 | 31 | 0.22 | 7 | 6% | | | | | |
| dissolved pellet 1 | 2.4 | 45.50 | 109 | 94% | 58.8 | 141 | 84% | 1.29 | 0.46 |
| dissolved pellet 2 | 2.1 | 1.10 | 2 | 2% | 1.7 | 3 | 2% | 1.52 | 0.03 |
| dissolved pellet 3 | 2.1 | 3.14 | 7 | 6% | 4.4 | 9 | 5% | 1.39 | 0.04 |
| dissolved pellet 4 | 2.1 | 10.70 | 22 | 19% | 15.6 | 33 | 19% | 1.46 | 0.11 |
| dissolved pellet 5 | 2.2 | 30.75 | 68 | 58% | 42.4 | 93 | 55% | 1.38 | 0.17 |
| dissolved pellet 6 | 2.2 | 50.05 | 110 | 95% | 64.7 | 142 | 85% | 1.29 | 0.19 |

TABLE 27

| | volume (mL) | VWF:Ag | | | VWF:RCo | | | Ratio |
| --- | --- | --- | --- | --- | --- | --- | --- | --- |
| | | conc. (IU/mL) | total (IU) | yield (%) | conc. (IU/mL) | total (IU) | yield (%) | RCo/Ag (IU/IU) |
| initial solution | 10500 | 2.5 | 26250 | 100% | 2.75 | 28875 | 100% | 1.10 |
| dissolved, diluted pellet | 2140 | 11.8 | 25252 | 96% | 12.95 | 27713 | 96% | 1.10 |

Example 15: Precipitation of Wild-Type vWF from Supernatant at Larger Scale

Recombinant von-Willebrand-factor wild-type was produced in phosphate-containing, synthetic CD-CHO-medium with CHO-cells as described in WO 2009/156137. The phosphate concentration was estimated to be about 4 mM/L.

380 mL 1 mol/L CaCl2+2H2O-solution was added to 9,000 mL cell-free supernatant with stirring at 25° C.-30° C. in a water bath. Accordingly, the final calcium concentration was about 40 mM/L. The addition of calcium took place within two minutes with mixing followed by an additional six minutes holding time without mixing. The precipitate was separated by a 30-minute centrifugation at 3,000×g.

The separated precipitate was dissolved at 37° C. in a buffer consisting of 20 mM/L HEPES and 120 mM/L EDTA. The resulting solution of 630 mL was diluted with a 10 mM//L HEPES+3 mM/L EDTA-solution to get to a conductivity of 8 mS/cm for subsequent chromatography.

Surprisingly the data in Table 28 show that the antigen yields of that purification are very high with 98% and the activity yield is still high with 91%. The VWF:RCoVWF:Ag ratio slightly decreased during precipitation. The final rVWF-WT has still good quality.

Example 15 also shows that the invention works for both VWF fusion proteins as well as for wild-type VWF.

Example 16: Precipitation of Plasma Derived VWF

Plasmatic VWF in the form of 300 mg NaCl-precipitate is dissolved in 300 mL PBS pH 7.2 containing 10 mM/L phosphate. The NaCl-Precipitate was gained by cryo precipitation of human plasma. After solving the cryoprecipitate an aluminum hydroxide adsorption step was performed to efficiently remove prothrombin and any other prothrombin complex factors. After that the main impurity fibrinogen was removed by precipitation with glycine. The resulting supernatant is precipitated by sodium chloride and that precipitate was used for this example.

12.5 mL of a 1 mol/L $CaCl_2+2H_2O$ solution was added to the 300 mL VWF-solution with stirring at 25° C.-30° C. in a water bath. Accordingly, the final calcium concentration was about 40 mM/L. The addition of calcium took about two minutes with mixing followed by an additional six minutes holding time without mixing. The precipitate was separated by a 30-minute centrifugation at 3.000×g. The separated precipitate was redissolved with 30 mL of a buffer consisting of 20 mM/L HEPES and 80 mM/L EDTA at a 37° C.

Surprisingly the results in Table 29 show that the yield of that purification is very high with 95% for antigen and 93% for activity. The VWF:RCo/VWF:Ag ratio during precipitation decreased very slightly. The final pVWF has still the same quality.

TABLE 28

| | volume (mL) | VWF:Ag | | | VWF:RCo | | | Ratio |
| --- | --- | --- | --- | --- | --- | --- | --- | --- |
| | | conc. (IU/mL) | total (IU) | yield (%) | conc. (IU/mL) | total (IU) | yield (%) | RCo/Ag (IU/IU) |
| initial solution | 9000 | 1.8 | 15840 | 100% | 1.60 | 14400 | 100% | 0.91 |
| dissolved, diluted pellet | 2000 | 7.7 | 15460 | 98% | 6.6 | 13140 | 91% | 0.85 |

TABLE 29

| description | volume (mL) | VWF:Ag | | | VWF:Rco | | | ratio |
| --- | --- | --- | --- | --- | --- | --- | --- | --- |
| | | conc. (IU/ml) | total (IU) | yield (%) | conc. (IU/ml) | total (IU) | yield (%) | RCo/Ag (IU/IU) |
| initial material | 300 | 4.3 | 1.284 | 100% | 3.61 | 1.084 | 100% | 0.84 |
| dis. pellet | 34 | 35.9 | 1.221 | 95% | 29.7 | 1.008 | 93% | 0.83 |

Example 16 also shows that the invention works also for a plasmatic vWF still comprising FVIII in complex with VWF as for both VWF fusion proteins and for wild-type VWF.

The invention claimed is:

1. A method for concentrating von Willebrand Factor (VWF) from an aqueous solution comprising the steps of
   (a) precipitating the VWF by adding calcium ions and phosphate ions to the aqueous solution,
   (b) separating the precipitate formed in step (a), and
   (c) resolubilizing the precipitate isolated in step (b) by contacting the precipitate with an aqueous solution comprising a calcium complexing agent, wherein
   the VWF comprises a full-length VWF polypeptide.

2. The method according to claim 1, wherein
   (i) the phosphate ions are at a concentration between 1 mM and less than 10 mM, and the calcium ions are at a concentration of at least 16 mM, or
   (ii) the phosphate ions are at a concentration of at least 10 mM, and the calcium ions are at a concentration of at least 10 mM.

3. The method according to claim 2, wherein the concentration of the phosphate ions is at most 50 mM.

4. The method according to claim 1, wherein the concentration of the phosphate ions is 5 mM and the concentration of the calcium ions is between 50 mM and 60 mM including the endpoints of that range.

5. The method according to claim 1, wherein the concentration of the calcium complexing agent ranges from at least 120 mM up to the limit of solubility of the calcium complexing agent.

6. The method according to claim 1, wherein the calcium complexing agent is EDTA or EGTA.

7. The method according to claim 1, wherein the aqueous solution used in step (c) is a buffer.

8. The method according to claim 1, wherein the temperature of the precipitation step ranges from 21° C. to 37° C.

9. The method according to claim 1, wherein the VWF:RCo/VWF:Ag ratio in the resolubilized precipitate is above 80% of the VWF:RCo/VWF:Ag ratio in the aqueous starting solution in step (a).

10. The method according to claim 1, wherein the yield of VWF:RCo in the resolubilized precipitate is at least 75%.

* * * * *